United States Patent [19]

Foster

[11] Patent Number: 4,607,111

[45] Date of Patent: Aug. 19, 1986

[54] PROCESS FOR SEPARATION OF TOCOPHEROL HOMOLOGUES (II)

[75] Inventor: Charles H. Foster, Kingsport, Tenn.

[73] Assignee: Eastman Kodak Company, Rochester, N.Y.

[21] Appl. No.: 736,904

[22] Filed: May 22, 1985

[51] Int. Cl.$^4$ .......................................... C07D 311/72
[52] U.S. Cl. ................................................... 549/413
[58] Field of Search .............................. 549/413, 410

[56] References Cited

U.S. PATENT DOCUMENTS 2,350,713 6/1944 Baxter ................................. 549/413
4,480,108 10/1984 Foster ................................. 549/413

Primary Examiner—Nicky Chan
Attorney, Agent, or Firm—Clyde L. Tootle; J. Frederick Thomsen

[57] ABSTRACT

A process for separating the α-tocopherol homologues from the other ester members of a tocopherol homologue mixture. The isolation of the α-tocopherol homologue is accomplished by selective deacylation of a mixture of tocopheryl esters in the presence of a base catalyst followed by separation of the α-ester from the other free tocopherols.

15 Claims, No Drawings

PROCESS FOR SEPARATION OF TOCOPHEROL HOMOLOGUES (II)

This invention relates to a process for separating the various tocopherol homologues from mixtures of the tocopherol homologues. The isolation of the various tocopherol homologues is accomplished by selective deacylation of all tocopheryl esters except the α-homologue followed by the separation of the α-homologue esters from the free tocopherols.

Heretofore, various processes have been used for separating and isolating the various tocopherol homologues, for example, α-tocopherol. One previous method for separating and isolating the various homologues has been accomplished by ion exchange chromatography, as noted in U.S. Pat. No. 3,402,182, or liquid chromatography. However, because of the very small differences in structure of the various tocopherol homologues, these separation processes require large quantities of adsorbent or resins. Also, these processes are useful mainly only for isolating δ-tocopherol from mixtures of α-, γ- and δ-tocopherol. Another process for separating the tocopherol homologues is disclosed in U.S. Pat. No. 4,480,108. This process uses a non-aromatic saturated amine to selectively deacylate one of the tocopherol homologues. While this is an excellent process, the process requires a fairly expensive cyclic amine which requires recovery and ultimate disposal. Therefore, it would be an advance in the state of the art to provide a more inexpensive, simple and efficient process for separation of the various tocopherol homologues from mixtures of such homologues.

In accordance with the present invention, it has been discovered that methanol, ethanol and n-propanol readily deacylate the β, γ- and δ-tocopheryl esters. However, the α-tocopheryl esters are relatively inert to such deacylation. Therefore, by merely reacting, in the presence of a particular base catalyst, a mixture of tocopheryl ester homologues with a primary alcohol containing 1 to 3 carbon atoms provides a mixture of δ-, β-, and γ-tocopherols with α-tocopheryl ester. The simple separation of the ester fraction from the tocopherol fraction by any of several methods (e.g., chromatography, ion exchange, distillation) leads to a separation of tocopherols and α-tocopheryl ester.

Generally, reacting the mixed tocopheryl acetates (α, β, γ, and δ) with methanol, ethanol, or n-propanol which, for example, is also a suitable solvent, in the presence of a particular base catalyst, at a temperature of about 40° C. to about 80° C., preferably 60° to 80° C., leads to rapid deacylation of δ-tocopheryl, β- and γ-tocopheryl but not the α-tocopheryl ester such as the acetate. The base catalyst can be, for example, potassium carbonate, potassium hydroxide or sodium hydroxide. The use of such catalyst enables the deacylation to be carried out at temperatures less than 100° C. by merely refluxing the alcohol solution and deacylating agent. The temperature of reaction can therefore be the boiling point of the alcohols. The reaction is carried out in an inert atmosphere. Since the polarity of the acetate is significantly different from that of the free tocopherol, this can allow the efficient chromatographic isolation of α-tocopheryl acetate. In addition, if one begins with a mixture that is mainly γ- and α-tocopheryl acetates (such as is obtained after removal of δ-tocopherol from natural tocopherol concentrates with basic ion-exchange resins followed by acetylation with acetic anhydride), methanol deacylation of γ-acetate 3 allows simple chromatographic purification of γ-tocopherol, 3b.

Scheme I

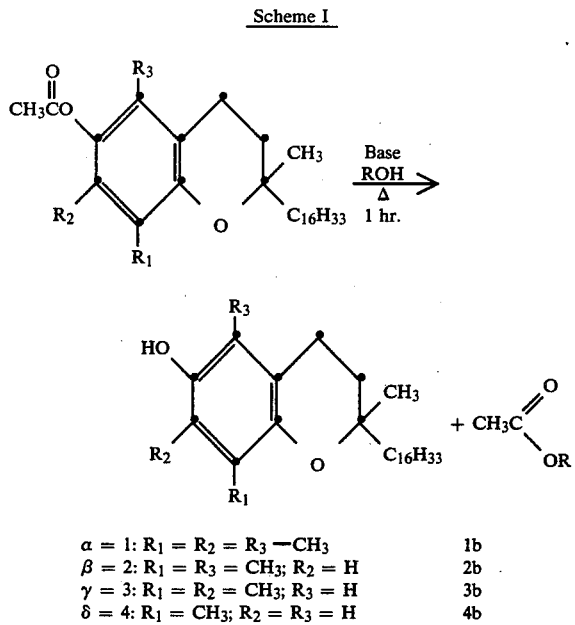

| α = 1: $R_1 = R_2 = R_3 = CH_3$ | 1b |
| β = 2: $R_1 = R_3 = CH_3$; $R_2 = H$ | 2b |
| γ = 3: $R_1 = R_2 = CH_3$; $R_3 = H$ | 3b |
| δ = 4: $R_1 = CH_3$; $R_2 = R_3 = H$ | 4b |

The reaction rate is dependent on the reaction temperature, the particular alcohol used, and the particular catalyst used. Methanol reacts faster than ethanol, and ethanol reacts faster than n-propanol, while secondary aliphatic alcohols such as isopropanol react too slowly to be useful. The amount of alcohol used is at least 1 mole to 1 mole tocopheryl acetate mixture, preferably with a large molar excess. The reaction is faster with sodium hydroxide than potassium carbonate which is faster than potassium hydroxide. In general, satisfactory results are obtained using about 0.01 to 0.2 molar amount of catalyst based on the amount of tocopheryl ester present in the distillate concentrate. However, greater or lesser amounts can be used depending on the particular catalyst and alcohol being used and the reaction rate desired.

This invention can be further illustrated by the following examples of preferred embodiments thereof, although it will be understood that these examples are included merely for purposes of illustration and are not intended to limit the scope of the invention unless otherwise specifically indicated.

EXAMPLE 1

About 10.0 g of a refined soybean oil distillate concentrate containing a mixture of tocopheryl acetates (7.5%, α; 0.77%; β; 21.15%; γ; 7.78%, δ) was mixed with 5 ml methanol and 15 mg of potassium carbonate added and heated at reflux for four hours. The mixture was cooled and the solvent removed by distillation. A GLPC analysis showed all of the δ-acetate, 94% of the γ-acetate and only 14% of the α-acetate had been converted to free tocopherols. The mixture can then be separated according to procedures well known in the art. The tocopherol ester fraction (now mostly α-tocopheryl acetate) can be converted to α-tocopherol by simple saponification.

EXAMPLE 2

Example 1 was repeated except that sodium hydroxide was used in place of potassium carbonate and refluxed for one hour instead of four hours. Essentially the same results were obtained as that of Example 1.

EXAMPLE 3

Example 1 was repeated except that potassium bicarbonate was used in place of potassium carbonate. A GLPC analysis showed that none of the tocopheryl acetates were converted to free tocopherols.

EXAMPLE 4

Example 3 was repeated except that sodium bicarbonate was used in place of potassium bicarbonate. Essentially the same results were obtained as that of Example 3.

EXAMPLE 5

Example 4 was repeated except that sodium carbonate was used in place of sodium bicarbonate. Essentially the same results were obtained as that of Example 4.

EXAMPLE 6

Example 5 was repeated except that calcium hydroxide was used in place of sodium carbonate. Essentially the same results were obtained as that of Example 5.

EXAMPLE 7

Example 1 was repeated except that 10 ml of EtOH was used in place of MeOH and the amount of potassium carbonate increased to 300 mg. After three hours GLPC analysis shows essentially the same results as that of Example 1 with no substantial increase of deacylation of the α-acetate.

EXAMPLE 8

Example 7 was repeated except that only 30 mg of potassium carbonate was used. After seven hours only 72% of the δ-acetate, 50% of the γ- and 3.1% of the α-acetate were deacylated. After 24 hours all of the δ-, γ-acetate and 18% of the α-acetate were deacylated.

EXAMPLE 9

A 30-gram sample of a mixture of tocopheryl acetates used in Example 1 and 30 ml of isopropanol and 1.0 g of potassium carbonate was heated at reflux for 22 hours. The solvent was removed by distillation. A GLPC analysis of the product showed none of the α-ester had deacylated and only 48% of the δ- and 28% of the γ-esters had deacylated.

The invention has been described in detail with particular reference to preferred embodiments thereof, but it will be understood that variations and modifications can be effected within the spirit and scope of the invention.

I claim:

1. A process for separating tocopherol homologues which comprises reacting a mixed α-, β-, γ, and δ-tocopheryl ester mixture with at least one alcohol of the group consisting of methanol, ethanol and n-propanol in the presence of a base catalyst comprising potassium carbonate, potassium hydroxide or sodium hydroxide at a temperature of about 40° C. to about 80° C. to deacylate tocopheryl esters other than the α-tocopheryl esters and separating the α-tocopherol ester from the deacylated homologues.

2. A process for isolating α-tocopheryl esters from the β-, γ, and δ-tocopheryl ester homologues according to claim 1 which comprises reacting the mixture of esters with at least one mole of at least one alcohol of the group consisting of methanol, ethanol and n-propanol in the presence of a base catalyst comprising potassium carbonate, potassium hydroxide or sodium hydroxide at a temperature of about 40° C. to about 80° C. to deacylate the β-, γ, and δ-tocopheryl esters, and thereafter separating the α-tocopheryl ester fraction from the tocopherol fraction.

3. A process for forming a mixture of β-, γ, and δ-tocopherol homologues and α-tocopheryl ester which comprises reacting a mixture of α-, β-, γ, and δ-tocopheryl esters with at least one alcohol of the group consisting of methanol, ethanol and n-propanol in the presence of a base catalyst comprising potassium carbonate, potassium hydroxide or sodium hydroxide at a temperature of about 40° C. to about 80° C. to deacylate tocopheryl esters other than the α-tocopheryl ester.

4. A process according to claim 2 wherein said alcohol is methanol.

5. A process according to claim 4 wherein said base is potassium carbonate.

6. A process according to claim 4 wherein said base is potassium hydroxide.

7. A process according to claim 4 wherein said base is sodium hydroxide.

8. A process according to claim 2 wherein said alcohol is ethanol.

9. A process according to claim 8 wherein said base is potassium carbonate.

10. A process according to claim 8 wherein said base is potassium hydroxide.

11. A process according to claim 8 wherein said base is sodium hydroxide.

12. A process according to claim 2 wherein said alcohol is n-propanol.

13. A process according to claim 12 wherein said base is potassium carbonate.

14. A process according to claim 12 wherein said base is potassium hydroxide.

15. A process according to claim 12 wherein said base is sodium hydroxide.

* * * * *